United States Patent
Kupferschmid et al.

(10) Patent No.: US 10,030,498 B2
(45) Date of Patent: Jul. 24, 2018

(54) METHOD AND SYSTEM FOR ADJUSTING THE POSITION OF AN OIL-WATER INTERFACE LAYER

(71) Applicant: FCCL PARTNERSHIP, Calgary (CA)

(72) Inventors: Denise M Kupferschmid, Calgary (CA); Glenn Price, Calgary (CA); Scott Yaholnitsky, Calgary (CA)

(73) Assignee: FCCL Partnership, Calgary (CA)

( * ) Notice: Subject to any disclaimer, the term of this patent is extended or adjusted under 35 U.S.C. 154(b) by 117 days.

(21) Appl. No.: 14/978,851

(22) Filed: Dec. 22, 2015

(65) Prior Publication Data

US 2016/0177695 A1 Jun. 23, 2016

Related U.S. Application Data

(60) Provisional application No. 62/096,457, filed on Dec. 23, 2014.

(51) Int. Cl.
*E21B 43/34* (2006.01)
*G01N 9/24* (2006.01)
(Continued)

(52) U.S. Cl.
CPC ............... *E21B 43/34* (2013.01); *G01N 9/24* (2013.01); *G01N 9/36* (2013.01); *G01N 23/12* (2013.01);
(Continued)

(58) Field of Classification Search
CPC .............. G01F 23/288; G01F 23/2885; G01N 2015/0668; G01N 23/10; G01N 23/12; G01N 23/125; G01N 23/14
(Continued)

(56) References Cited

U.S. PATENT DOCUMENTS

| | | | | | |
|---|---|---|---|---|---|
| 2,216,977 A | * | 10/1940 | Mahone | ................... | G05D 9/12 137/172 |
| 3,220,930 A | * | 11/1965 | Thompson | ............. | C10G 33/02 196/132 |

(Continued)

FOREIGN PATENT DOCUMENTS

| | | |
|---|---|---|
| JP | H59-150509 | 8/1984 |
| JP | H02-098582 | 4/1990 |

(Continued)

OTHER PUBLICATIONS http://www.vega.com/downloads/ohmart/(CPB)%20Customer%20Product%20Brochures/35237-US.pdf, last accessed Jul. 8, 2014.

(Continued)

*Primary Examiner* — Mary McManmon
*Assistant Examiner* — Richard K Durden

(57) ABSTRACT

A system and method for adjusting a position of an oil-water interface layer. A vessel, such as a free water knockout or a treater used in the processing of heavy oil, contains a fluid comprising the interface layer. A nuclear densitometer is positioned to obtain density measurements of the fluid at various heights along the vessel. Based at least in part on these density readings, a valve controlling flow out of a water discharge port on the vessel may be actuated, with the flow of water through the water discharge port being inversely proportional to the height of the interface layer.

16 Claims, 10 Drawing Sheets

(51) Int. Cl.
  *G01N 9/36*   (2006.01)
  *G01N 23/12*  (2018.01)
  *G05D 9/12*   (2006.01)
  *G05D 11/13*  (2006.01)
  *G01N 33/18*  (2006.01)
  *G01N 15/06*  (2006.01)
  *G01F 23/288* (2006.01)
  *G01N 33/28*  (2006.01)

(52) U.S. Cl.
  CPC ........... *G05D 9/12* (2013.01); *G01F 23/2885* (2013.01); *G01N 33/1833* (2013.01); *G01N 33/2823* (2013.01); *G01N 33/2847* (2013.01); *G01N 2015/0668* (2013.01); *G05D 11/132* (2013.01); *G05D 11/137* (2013.01)

(58) Field of Classification Search
  USPC ........... 73/61.43, 64.55; 137/88, 91, 92, 172
  See application file for complete search history.

(56) References Cited

U.S. PATENT DOCUMENTS

| | | | |
|---|---|---|---|
| 3,346,508 A | 10/1967 | Thompson | |
| 3,594,575 A * | 7/1971 | Shoemaker | G01F 23/2885 378/52 |
| 3,849,285 A | 11/1974 | Prestridge | |
| 6,548,814 B1 * | 4/2003 | Gronli | G01N 23/04 250/357.1 |
| 6,633,625 B2 | 10/2003 | Jackson | B01D 17/00 250/357.1 |
| 7,986,766 B2 | 7/2011 | Cahill | |
| 8,171,785 B2 * | 5/2012 | Aasheim | G01F 23/0076 73/290 R |
| 8,495,913 B2 * | 7/2013 | Partington | G01F 23/2961 73/290 V |
| 8,792,611 B2 * | 7/2014 | Cahill | G01F 23/288 378/52 |
| 9,274,247 B1 * | 3/2016 | Hewitson | G01N 23/125 |
| 2003/0117150 A1 * | 6/2003 | Noik | B01D 19/0063 324/639 |
| 2005/0250860 A1 * | 11/2005 | Appleford | B01D 17/0208 516/135 |
| 2008/0142414 A1 * | 6/2008 | Gramme | B01D 17/0214 208/188 |
| 2011/0048125 A1 * | 3/2011 | Jackson | G01F 23/2885 73/290 R |
| 2013/0082010 A1 | 4/2013 | Al-Mulhim et al. | |
| 2013/0087715 A1 * | 4/2013 | Cahill | G01F 23/2885 250/393 |
| 2014/0251874 A1 * | 9/2014 | Barroeta | C10G 31/08 208/298 |
| 2014/0316734 A1 * | 10/2014 | Kulik | G01N 9/00 702/100 |
| 2015/0168317 A1 * | 6/2015 | Koernle | G01N 23/10 378/54 |
| 2016/0008742 A1 * | 1/2016 | Adler | B01D 19/0063 96/157 |

FOREIGN PATENT DOCUMENTS

| | | |
|---|---|---|
| JP | H06-341968 | 12/1994 |
| JP | H07-109955 | 4/1995 |
| JP | H08-282798 | 10/1996 |
| JP | H10-174802 | 6/1998 |
| JP | 2000-283826 | 10/2000 |
| JP | 2012205987 | 10/2012 |
| WO | 2002/098787 | 12/2002 |
| WO | 2010/134821 | 11/2010 |

OTHER PUBLICATIONS

Mahmoud Meribout, Ahmed Al Naamany and Khamis Al Busaidi (2011). Interface Layers Detection in Oil Field Tanks: A Critical Review, Expert Systems for Human, Materials and Automation, Prof. Petrică Vizureanu (Ed.), ISBN: 978-953-307-334-7, InTech, Available from: http://www.intechopen.com/books/expert-systemsfor-human-materials-and-automation/interface-layers-detection-in-oil-field-tanks-a-critical-review.

* cited by examiner

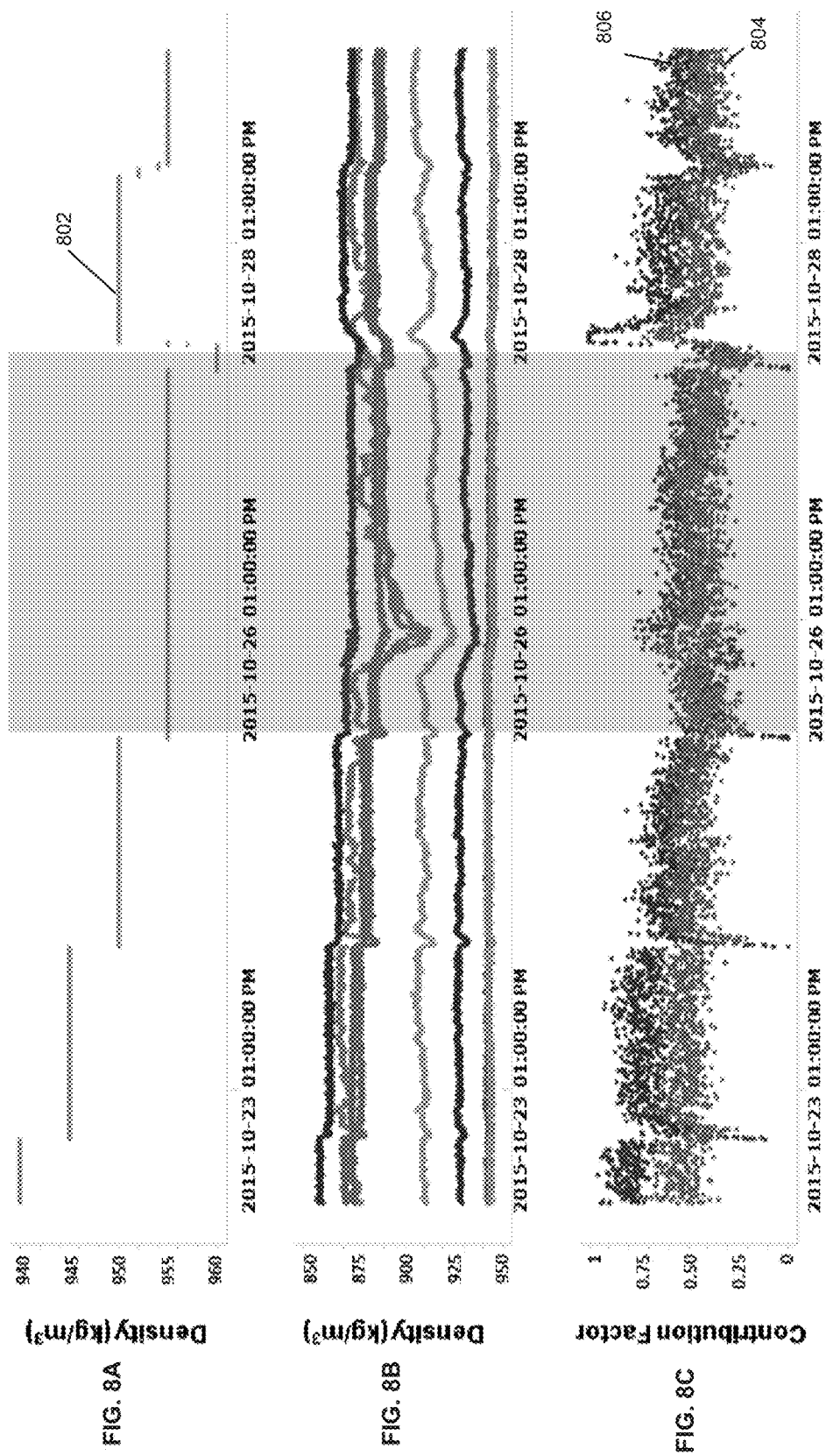

METHOD AND SYSTEM FOR ADJUSTING THE POSITION OF AN OIL-WATER INTERFACE LAYER

TECHNICAL FIELD

The present disclosure is directed at methods, systems, and techniques for adjusting the position of an oil-water interface layer.

BACKGROUND

Producing oil from unconventional hydrocarbon deposits such as the Canadian oil sands presents challenges materially different from those encountered during conventional oil production. The highly viscous bitumen comprising the oil sands, for example, requires significant treatment in order to sufficiently lower its density and viscosity to permit production. Given the vast economic potential the Canadian oil sands and other similar hydrocarbon deposits represent, research and development continue into methods, systems, and techniques related to unconventional oil production.

SUMMARY

According to a first aspect, there is provided a method for adjusting a position of an oil-water interface layer. The method comprises obtaining, from a nuclear densitometer positioned to emit radiation at one or more known heights into a vessel containing a fluid comprising the interface layer and to measure the radiation after it has passed through the fluid, one or more density measurements of the fluid at the one or more known heights; and in response to the one or more density measurements, increasing or decreasing flow through a water discharge port comprising part of the vessel.

The nuclear densitometer may comprise at least one nuclear source extending vertically along one of an inside or outside of the vessel and one or more nuclear detectors located on the other of the inside or outside of the vessel at the known heights.

The method may further comprise comparing at least one of the density measurements to a water discharge density setpoint; and when any of the at least one of the density measurements is less than the density setpoint, decreasing the flow through the water discharge port.

The method may further comprise for each of at least one of the density measurements, comparing the density measurement to a water discharge density setpoint specific to the detector used to obtain the density measurement ("detector-specific density setpoint"); and decreasing the flow through the water discharge port in response to how much each of the density measurements is less than the detector-specific density setpoint.

Each of the detectors used to obtain the density measurements may be associated with a weight ("detector-specific weight") directly proportional to the degree the density measurement obtained using the detector influences the flow through the water discharge port.

Each of the detectors used to obtain the density measurements may be associated with a density range ("detector-specific density range") inversely proportional to the degree the density measurement obtained using the detector influences the flow through the water discharge port when the density measurement deviates from the detector-specific density setpoint by less than the detector-specific density range. The density measurement obtained using the detector need not influence the flow through the water discharge port when the density measurement deviates from the detector-specific density setpoint by at least the detector-specific density range.

The density measurements may be obtained using n different detectors and the flow through the water discharge port may be reduced proportionally to $$\sum_{i=1}^{n} \text{Weight}_i \times \text{MIN}\left[1, \text{MAX}\left[0, \frac{SP_i - \text{Density}_i}{\text{Range}_i}\right]\right],$$

wherein $\text{Weight}_i$ is the detector-specific weight for detector i, $SP_i$ is the detector-specific density setpoint for detector i, $\text{Density}_i$ is the density measurement obtained using detector i, and $\text{Range}_i$ is the detector-specific density range for detector i.

$\Sigma_i \text{Weight}_i$ may be equal to 1.

The detector-specific density setpoint may be determined from an initial detector-specific density setpoint, determined at a previous calibration, that is offset by a value proportional to a difference between a current temperature of the vessel and a temperature of the vessel obtained at the previous calibration.

The detectors used to obtain the density measurements may comprise a continuous series of one or more detectors including a bottommost detector located above the water discharge port.

The method may further comprise comparing at least one of the density measurements to a sales oil density setpoint; and when any of the at least one density measurements is greater than the sales oil density setpoint, increasing the flow through the water discharge port.

Obtaining a density measurement may be performed using an electrostatic grid located within and at the top of the vessel containing the fluid.

The method may further comprise for each of at least one of the density measurements, comparing the density measurement to a sales oil density setpoint specific to the detector used to obtain the density measurement; and increasing the flow through the water discharge port in response to how much each of the density measurements is greater than the detector-specific density setpoint.

Each of the detectors used to obtain the density measurements may be associated with a weight directly proportional to the degree the density measurement obtained using the detector influences the flow through the water discharge port.

Each of the detectors used to obtain the density measurements may be associated with a density range inversely proportional to the degree the density measurement obtained using the detector influences the flow through the water discharge port when the density measurement deviates from the detector-specific density setpoint by less than the detector-specific density range. The density measurement obtained using the detector need not influence the flow through the water discharge port when the density measurement deviates from the detector-specific density setpoint by at least the detector-specific density range.

The density measurements may be obtained using n different detectors and the flow through the water discharge port may be increased proportionally to $$\sum_{j=1}^{n} \text{Weight}_j \times \text{MIN}\left[1, \text{MAX}\left[0, \frac{\text{Density}_j - SP_j}{\text{Range}_j}\right]\right],$$

wherein Weight$_j$ is the detector-specific weight for detector j, SP$_j$ is the detector-specific density setpoint for detector j, Density$_j$ is the density measurement obtained using detector j, and Range$_j$ is the detector-specific density range for detector j.

$\Sigma_j$ Weight$_j$ may be equal to 1.

The detectors used to obtain the density measurements may comprise a continuous series of one or more detectors including a topmost detector.

For the upper detectors, the detector-specific density setpoint may be determined from an initial detector-specific density setpoint, determined at a previous calibration, that is offset by a value proportional to one or both of a difference between a current temperature of the vessel and a temperature of the vessel obtained at the previous calibration; and a current density of oil exiting the vessel and a density of oil exiting the vessel obtained at the previous calibration.

The nuclear detectors may comprise lower and upper detectors, and at least one of the density measurements obtained using the upper detectors may be used to determine whether to increase the flow through the water discharge port and at least one of the density measurements obtained using the lower detectors may be used to determine whether to decrease the flow through the water discharge port.

The lower detectors may comprise a continuous series of one or more detectors including a bottommost detector located above the water discharge port and the upper detectors may comprise a continuous series of one or more detectors including a topmost detector.

The upper detectors and lower detectors may be exclusive of each other.

The method may further comprise for each of the upper and lower detectors, comparing the density measurement to a density setpoint specific to the detector used to obtain the density measurement; and increasing or decreasing the flow through the water discharge port in response to how much each of the density measurements obtained using the lower detectors is less than the detector-specific density setpoint, and how much each of the density measurements obtained using the upper detectors is greater than the detector-specific density setpoint.

Each of the detectors used to obtain the density measurements may be associated with a weight directly proportional to the degree the density measurement obtained using the detector influences the flow through the water discharge port.

Each of the detectors used to obtain the density measurements may be associated with a density range inversely proportional to the degree the density measurement obtained using the detector influences the flow through the water discharge port when the density measurement deviates from the detector-specific density setpoint by less than the detector-specific density range. The density measurement obtained using the detector need not influence the flow through the water discharge port when the density measurement deviates from the detector-specific density setpoint by at least the detector-specific density range.

The density measurements may be obtained using $n_{lower}$ different lower detectors and $n_{upper}$ upper detectors, and the flow through the water discharge port may be modified by a factor proportional to $$\left[1 - \sum_{i=1}^{n\_lower} \text{Weight}_i \times \text{MIN}\left[1, \text{MAX}\left[0, \frac{SP_i - \text{Density}_i}{\text{Range}_i}\right]\right]\right] \cdot \left[1 + \right.$$

-continued $$\left. \sum_{j=1}^{n\_upper} \text{Weight}_j \times \text{MIN}\left[1, \text{MAX}\left[0, \frac{\text{Density}_j - SP_j}{\text{Range}_j}\right]\right]\right],$$

wherein Weight$_{i/j}$ is the detector-specific weight for detector i/j, SP$_{i/j}$ is the detector-specific density setpoint for detector i/j, Density$_{i/j}$ is the density measurement obtained using detector i/j, and Range$_{i/j}$ is the detector-specific density range for detector i/j.

$\Sigma_i$ Weight$_i$ and $\Sigma_j$ Weight$_j$ may each be equal 1.

The detector-specific density setpoint may be determined from an initial detector-specific density setpoint, determined at a previous calibration, that is offset by a value proportional to a difference between a current temperature of the vessel and a temperature of the vessel obtained at the previous calibration.

For the upper detectors, the detector-specific density setpoint may be determined from an initial detector-specific density setpoint, determined at a previous calibration, that is offset by a value proportional to one or both of a difference between a current temperature of the vessel and a temperature of the vessel obtained at the previous calibration; and a current density of oil exiting the vessel and a density of oil exiting the vessel obtained at the previous calibration.

According to another aspect, there is provided a system for adjusting a position of an oil-water interface layer. The system comprises a vessel for containing a fluid comprising the oil-water interface layer and comprising a water discharge port and a fluid outlet, the fluid outlet being higher on the vessel than the water discharge port; a nuclear densitometer positioned to emit radiation into the fluid and to measure the radiation after it has passed through the fluid, wherein the radiation passes through the fluid at one or more known heights of the fluid; a water discharge valve positioned to control flow through the water discharge port; a controller communicatively coupled to the nuclear densitometer and to the water discharge valve, the controller configured to perform a method for adjusting a position of an oil-water interface layer. The method may comprise (i) obtaining, from the nuclear densitometer, one or more density measurements at the one or more known heights at which the radiation passed through the fluid; and (ii) in response to the one or more density measurements, increasing or decreasing flow through the water discharge port by actuating the water discharge valve. Alternatively, the method may comprise any aspects of the method described above or suitable combinations thereof.

According to another aspect, there is provided an apparatus for adjusting a position of an oil-water interface layer. The apparatus comprises a controller, which comprises a processor; and a non-transitory computer readable medium communicatively coupled to the controller and having stored thereon program code that, when executed by the processor, causes the processor to perform any aspects of the method described above or suitable combinations thereof.

According to another aspect, there is provided a non-transitory computer readable medium having stored thereon program code that, when executed by a processor, causes the processor to perform any aspects of the method described above or suitable combinations thereof.

According to another aspect, the interface layer need not be an oil-water interface layer, but instead may be an interface layer of two other fluids of different densities. Those two fluids may be normally immiscible and enter the vessel emulsified.

This summary does not necessarily describe the entire scope of all aspects. Other aspects, features and advantages will be apparent to those of ordinary skill in the art upon review of the following description of specific embodiments.

BRIEF DESCRIPTION OF THE DRAWINGS

In the accompanying drawings, which illustrate one or more example embodiments:

FIGS. 8A-8C are graphs depicting density of the oil exiting the vessel, density measurements obtained using another embodiment of the system for adjusting the position of an oil-water interface layer installed on the vessel, and contribution made by various of the density measurements to the determination of how to adjust flow through the vessel's water discharge port.

DETAILED DESCRIPTION

Figure 1:
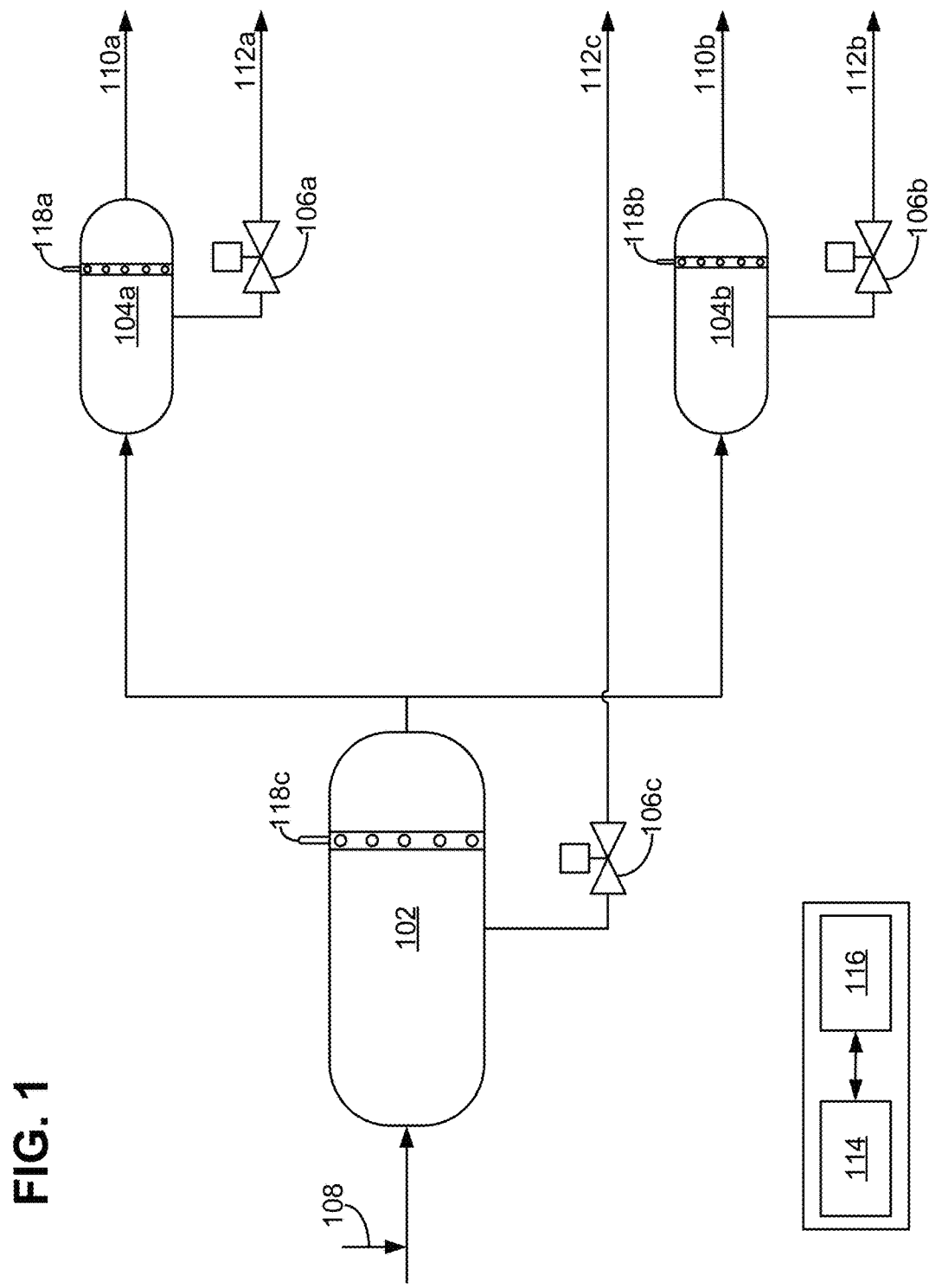
FIG. 1 is a block diagram of a plant comprising a free water knockout and two treaters, each of which has installed on it a nuclear densitometer comprising part of a first embodiment of a system for adjusting the position of an oil-water interface layer.

Directional terms such as "top", "bottom", "upwards", "downwards", "vertically", and "laterally" are used in the following description for the purpose of providing relative reference only, and are not intended to suggest any limitations on how any article is to be positioned during use, or to be mounted in an assembly or relative to an environment. Additionally, the term "couple" and variants of it such as "coupled", "couples", and "coupling" as used in this description are intended to include indirect and direct connections unless otherwise indicated. For example, if a first device is coupled to a second device, that coupling may be through a direct connection or through an indirect connection via other devices and connections. Similarly, if the first device is communicatively coupled to the second device, communication may be through a direct connection or through an indirect connection via other devices and connections.

One process used to produce oil from unconventional hydrocarbon deposits such as those comprising the Canadian oil sands is steam-assisted gravity drilling ("SAGD"). In SAGD, two closely spaced and parallel wells are drilled: an injector well and a producer well, with the injector well located above the producer well. Steam is injected into the injector well, which heats the bitumen in the region between the two wells. The heated bitumen flows into the producer well and is pumped to the surface.

Given the use of steam during production, the produced crude oil is in the form of an oil-water emulsion. Equipment such as free water knockouts (each an "FWKO") and treaters are used to separate the oil from the water, with the oil being sold and the water eventually being returned to the environment. Significant technical challenges arise when attempting to separate the oil and water that comprise the oil-water emulsion from each other because the interface layer comprising the emulsion is often ill defined.

The prior art includes several techniques for attempting to separate the oil and water comprising the oil-water emulsion from each other. For example, light hydrocarbons known as diluent are injected into the emulsion feeding the FWKO and treaters; the diluent lowers the density of the oil aiding in gravity separation of the oil and water phases of the emulsion. However, using diluent is associated with drawbacks. For example, the concentration of hydrocarbons in the diluent is estimated based on long-term emulsion sampling and is not typically changed to reflect real-time changes in emulsion composition. Additionally, adding diluent is a type of chemical treatment and can therefore pose environmental issues and impose financial costs.

The embodiments described herein use a nuclear densitometer that samples the density of fluid at various known positions within a vessel; more particularly, the depicted embodiments use a nuclear densitometer that samples the density of fluid at various known heights within a vessel such as an FWKO or a treater. As oil is less dense than water, the density reading obtained at each of these heights indicates whether the fluid at that height is oil (e.g., sales oil, of which one example is dilbit), water, or a mixture of oil and water, which represents the oil-water emulsion comprising the interface layer. From these density readings, a processor actuates a water discharge valve that is fluidly coupled to a water discharge port on an underside of the vessel. When the water discharge valve is open, the fluid (preferably primarily or entirely water) exits the vessel and the interface layer lowers. When the water discharge valve is closed, relatively pure water is allowed to settle at the bottom of the vessel for subsequent release, which increases the height of the interface layer. An electrostatic grid may be positioned at or near the top of the vessel to promote oil dehydration. As alluded to above as used herein, a reference to "water" being discharged from the vessel includes but is not limited to pure water, and includes water that is contaminated by contaminants, such as hydrocarbons; in some embodiments, while the discharged water is contaminated, it is sufficiently pure to be discharged to environment in accordance with applicable environmental legislation.

Referring now to FIG. 1, there is shown a block diagram of a plant comprising an FWKO 102 fluidly coupled in parallel to two treaters 104a,b (collectively, "treaters 104"). Each of the FWKO 102 and the treaters 104 has installed on it a nuclear densitometer 118a-c (collectively, "nuclear densitometers 118") that comprises part of a first embodiment of a system for adjusting the position of an oil-water interface layer E (shown in FIG. 2A). As discussed in more detail below in respect of FIGS. 2A and 2B, each of the nuclear densitometers 118 in this first embodiment permits density readings to be obtained at positions comprising five different heights $h_1$-$h_5$ (shown at FIG. 2A) at a given longitudinal position along the FWKO 102 or the treaters 104.

Figure 2A:
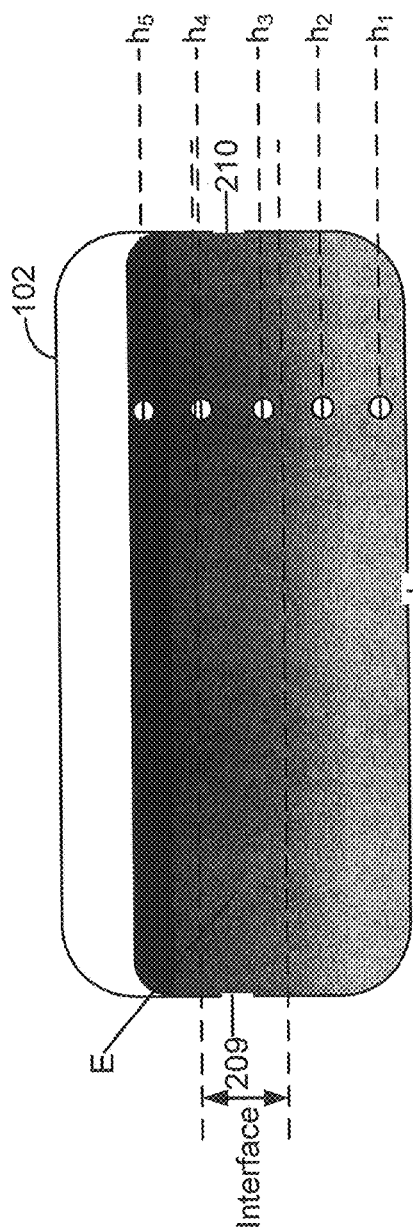
FIGS. 2A and 2B are orthogonal sectional views of the free water knockout of FIG. 1.

The FWKO 102 comprises an emulsion inlet 209, an emulsion outlet 210, and a water discharge port 202 (the inlet, outlet, and port 209,210,202 are shown in FIG. 2A). A diluent conduit 108 is fluidly coupled to the emulsion inlet 209 and permits diluent to be added to the emulsion entering the FWKO 102 to assist in separation of oil and water. Fluidly coupled to and positioned to control flow through the water discharge port 202 is a water discharge valve 106c. The water discharge port 202 is located on an underside of the FWKO 102 so that water that has settled on to the bottom of the FWKO 102 can be emptied from the FWKO 102 by opening the water discharge valve 106c. Fluid exiting the water discharge port 202 via the water discharge valve 106c is directed along a water discharge port conduit 112c. Although not depicted in FIG. 1, in an alternative embodiment there may be an additional emulsion outlet valve that is fluidly coupled to and can be used to control the flow rate of the emulsion exiting the FWKO 102 via the emulsion outlet 210.

Each of the treaters 104 similarly comprises an emulsion inlet, an oil outlet (analogous to the emulsion outlet 210 of the FWKO 102), and a water discharge port. Water discharge valves 106a,b are fluidly coupled to and positioned to control flow through the treaters' 104 water discharge ports. As with the FWKO 102, each of the treaters' 104 water discharge ports is located on the treater's 104 underside so that water that has settled to the bottom of the treaters 104 can be discharged by opening the water discharge valves 106a,b. Fluid exiting the treaters' 104 water discharge ports is directed along additional water conduits 112a,b. Each of the treaters' 104 emulsion inlets is fluidly coupled to the FWKO's 102 emulsion outlet 210. Fluid exiting the oil outlets is, for example, sales oil comprising suitably low volumes of water; this fluid is directed along sales oil conduits 110a,b. Although not depicted in FIG. 1, in an alternative embodiment one or both of the treaters 104 may comprise an oil outlet valve fluidly coupled to and positioned to control flow through the treaters' 104 oil outlets. The FWKO's 102 emulsion outlet 210 and the treaters' 104 oil outlets are examples of fluid outlets of vessels to which the system 100 may be installed.

The FWKO 102 also comprises flow meters measuring the flow rate of the emulsion into and out of the FWKO 102, and a level meter monitoring the height of the fluid within the FWKO 102. Each of the treaters 104 also comprises analogous meters.

FIG. 1 also shows a processor 114 communicatively coupled to a non-transitory computer readable medium 116 that stores program code that, when executed by the processor 114, causes the processor 114 to perform an embodiment of a method for adjusting the position of an oil-water interface layer, as described in further detail below with respect to FIGS. 4 and 5; the processor 114 and computer readable medium 116 collectively comprise an example system controller. The controller further comprises input/output (IO) circuitry (not depicted) that is communicatively coupled to the processor 114 and that permits the processor 114 to communicate with the various sensors and actuators of the system 100. In the depicted embodiment, the processor 114 is wirelessly communicatively coupled to all the nuclear densitometers 118 and to the water discharge valves 106a-c (collectively, "water discharge valves 106") and is able to retrieve density measurements from the nuclear densitometers 118 and to control each of the water discharge valves 106 independently; however, in alternative embodiments (not depicted), any number of the nuclear densitometers 118 and water discharge valves 106 may be communicative with and controlled by different processors 114. Additionally, although the IO circuitry communicates with the various components of the system 100 wirelessly in FIG. 1, in alternative embodiments (not depicted) communication may be wireline.

Additionally, the FWKO 102 and treaters 104 are shown as each comprising a single water discharge valve 106 and being outfitted with a single nuclear densitometer 118. In alternative embodiments (not depicted), however, the FWKO 102 and treaters 104 may each comprise multiple water discharge valves 106 and may be outfitted with multiple nuclear densitometers 118 in order to obtain density measurements at various locations along their lengths. For example, in one non-depicted alternative embodiment, the FWKO 102 may comprise one water discharge valve 106 located a quarter of the FWKO's 102 length from one end and another water discharge valve 106 located a quarter of the FWKO's 102 length from the opposing end, with a different nuclear densitometer 118 positioned near each of the water discharge valves 106. The processor 114 may then control the water discharge valves 106 in response to measurements obtained using the nearer nuclear densitometer 118.

Figure 2B:
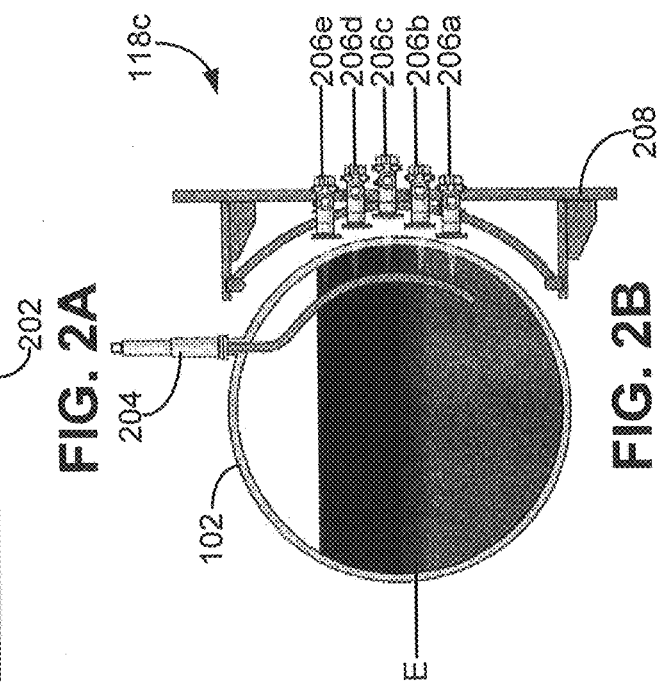

Referring now to FIGS. 2A and 2B, there are shown sectional views of the FWKO 102 taken along planes extending parallel and traverse to the longitudinal axis of the FWKO 102, respectively. While FIGS. 2A and 2B depict the FWKO 102, the analogous sectional views for the treaters 104 are substantially similar. The sectional view of FIG. 2A is taken looking parallel to the direction of propagation of the radiation that the nuclear densitometers 118 emit.

In FIGS. 2A and 2B, the majority of the FWKO 102 is filled with production fluid. The production fluid comprises the emulsion (i.e., the oil-water interface layer E) above which is primarily oil (e.g., sales oil or dilbit), shown in darker contrast in FIGS. 2A and 2B, and below which is primarily water, shown in lighter contrast in FIGS. 2A and 2B. Each of the nuclear densitometers 118 comprises a frame 208 outside of the FWKO 102 or treater 104 on which is mounted five nuclear detectors 206a-e (collectively, "nuclear detectors 206") at five different positions on the FWKO 102 or treater 104; the positions in the depicted embodiment correspond to heights on the FWKO 102 or treater 104. While the depicted embodiment comprises five of the nuclear detectors 206, in alternative embodiments (not depicted) more or fewer than five of the detectors 206 may be used, as may be necessary or desirable for a particular installation. In FIGS. 2A and 2B, the bottommost detector 206a is located at height $h_1$ above the bottom of the FWKO 102; the second detector 206b is located at height $h_2$; the third detector 206c is located at height $h_3$; the fourth detector 206d is located at height $h_4$; and the uppermost detector 206e is located at height $h_5$, with $h_1 < h_2 < h_3 < h_4 < h_5$ as measured from the bottom of the FWKO 102. At least one nuclear source 204 extends through FWKO's 102 wall and includes a portion that extends vertically inside the FWKO 102. The detectors 206 in this embodiment are similarly mounted on each of the treaters 104. When in operation, the nuclear source 204 emits radiation at at least $h_{1-5}$, and the amount of radiation that the detectors 206 receive is inversely proportional to the density of the production fluid at $h_{1-5}$. In the depicted embodiment, the sales oil has a density of approximately 840 kg/m³, the water that is suitable for discharging has a density of approximately 940 kg/m³, and the oil-water interface layer E has a density between approximately 840 kg/m³ and 940 kg/m³. Each of the detectors 206 obtains a density measurement of the portion of the production fluid located between the nuclear source 204 and that detector 206 and sends that density reading to the processor 114 when active. In an alternative embodiment (not depicted), multiple nuclear densitometers 118 may be deployed at or about the same longitudinal position along the FWKO 102 or another vessel to which the system 100 has been mounted. For example, in a relatively wide vessel one of the nuclear densitometers 118 may be mounted to one side of the vessel at one longitudinal position and the other of the nuclear densitometers 118 may be mounted to an opposite side of the vessel at the same longitudinal position, with each of the two densitometers 118 providing density readings for the fluid located in the half of the vessel to which it is mounted.

While in the depicted embodiment the at least one nuclear source 204 is within the vessel and the detectors 206 are outside the vessel, alternative embodiments (not depicted) are possible. For example, the at least one nuclear source 204 may be outside the vessel and the detectors 206 may be inside the vessel. Additionally or alternatively, instead of the detectors 206 being physically discrete, the detectors 206 may comprise different detection areas on a shared substrate.

An electrostatic grid (not shown) is located within and near the top of each of the treaters 104, above the uppermost detector 206e. The electrostatic grid is communicatively coupled to the processor 114, with the processor 114 monitoring the voltage level of the electrostatic grid; in the depicted embodiment, the voltage of the grid can vary from 0 V to 15,000 V. The voltage of the grid varies in response to the water content of the fluid near the grid, and more particularly voltage magnitude increases as density of the fluid near the grid decreases (i.e., as the interface layer lowers) and decreases as density of the fluid near the grid increases (i.e., as the interface layer rises).

Figure 3A:
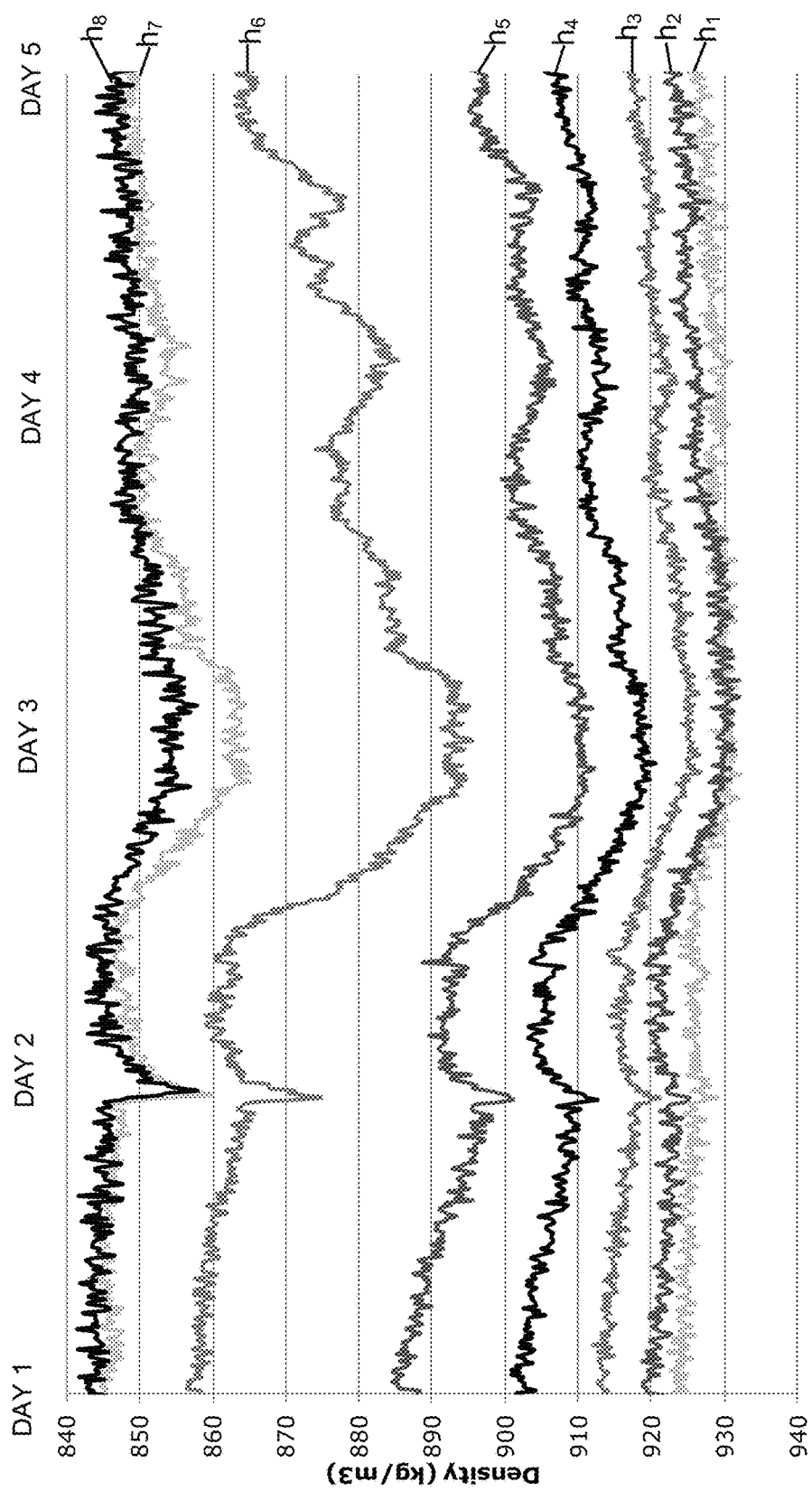
FIG. 3A is a graph showing density measurements obtained over a five day period using a second embodiment of the system for adjusting the position of an oil-water interface layer installed on a vessel.
Figure 3B:
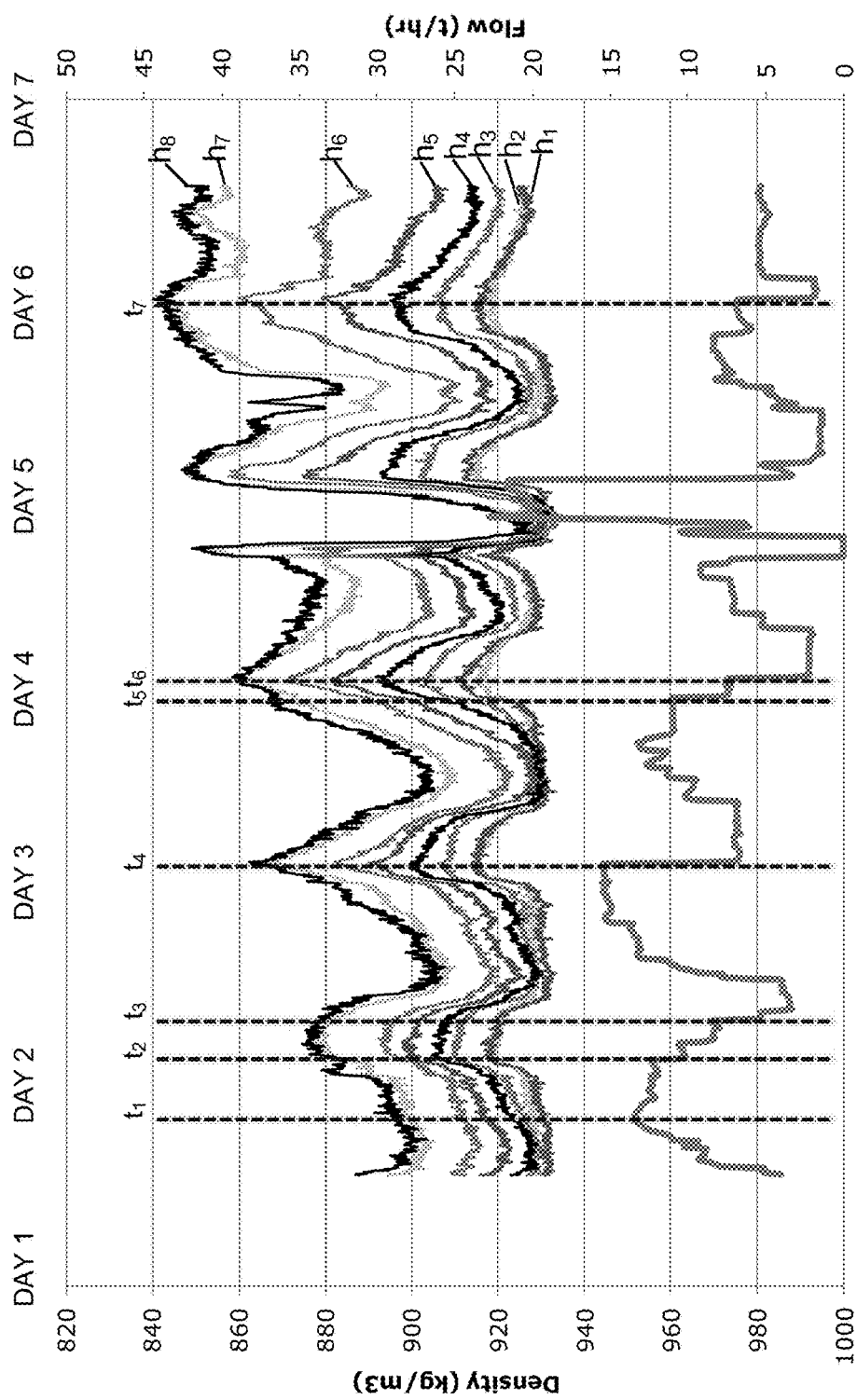
FIG. 3B is a graph illustrating how the height of an interface layer varies in response to flow through a water discharge valve in the vessel.
Figure 3C:
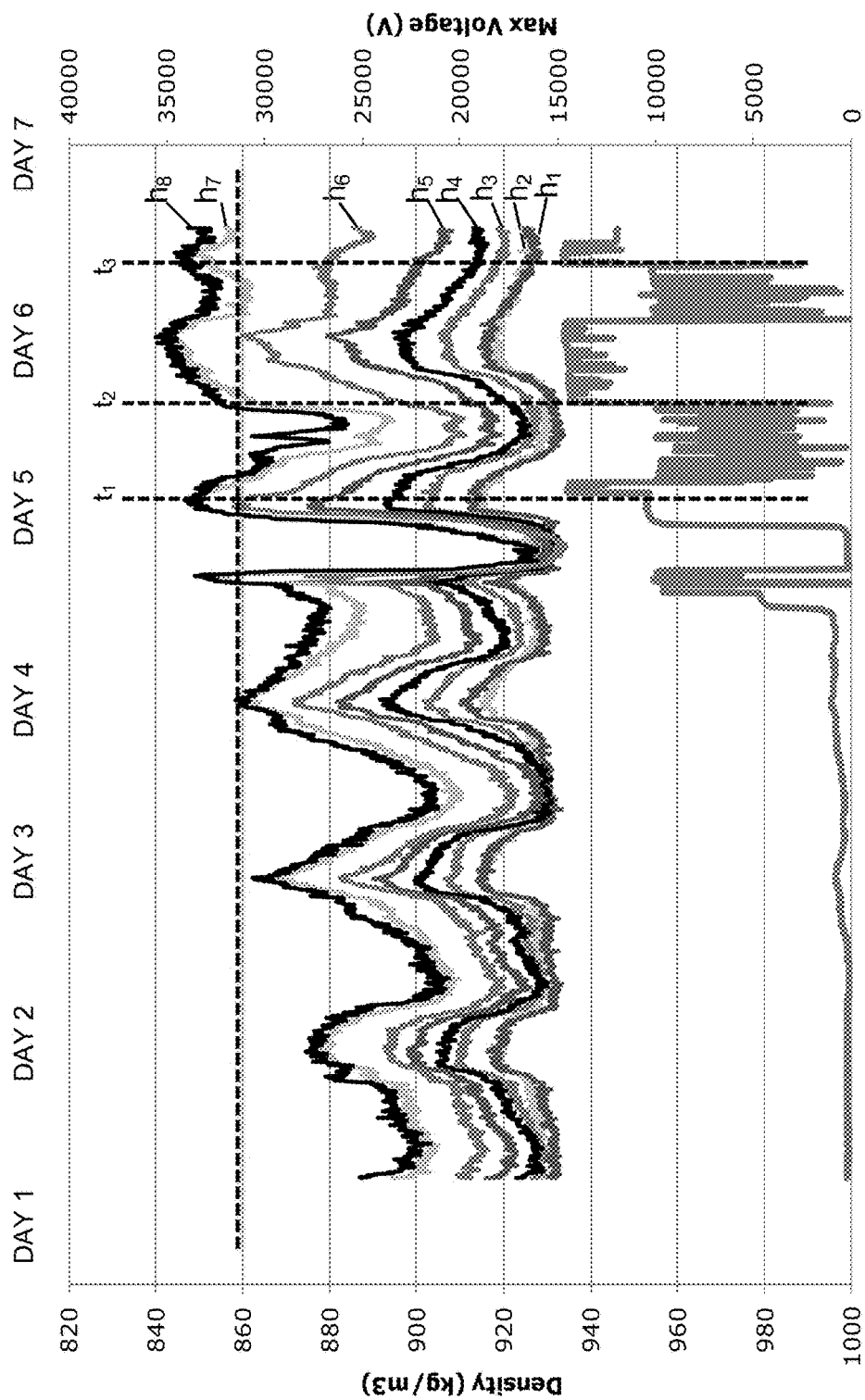
FIG. 3C is a graph illustrating how the height of an interface layer corresponds to voltage measured across an electrostatic grid contained within the vessel.

Referring now to FIGS. 3A-3C, there are shown graphs of density measurements using an embodiment of the nuclear densitometer 118 that comprises eight detectors 206 located at heights $h_1$-$h_8$, with the height of the water discharge port 202<$h_1$, the height of the electrostatic grid>$h_8$, and $h_1$=600 mm, $h_2$=800 mm, $h_3$=1,000 mm, $h_4$=1,200 mm, $h_5$=1,400 mm, $h_6$=1,600 mm, $h_7$=1,800 mm, and $h_8$=2,000 mm.

In FIG. 3A, the nuclear densitometer 118 monitors the density of the fluid within the treater 104 over a period of four days. The density observations reveal that the fluid is fairly stable, with the interface layer E being located at heights $h_4$-$h_6$, the portion of the fluid comprising primarily oil being located at heights $h_7$ and $h_8$, and the portion of the fluid comprising primarily water being located at heights $h_1$-$h_3$.

In FIG. 3B, the nuclear densitometer 118 monitors the density of the fluid within the treater 104 over a period spanning approximately six days. During this time, as shown in FIG. 3B, the processor 114 actuates the water discharge valve 106c such that flow through the water discharge port 202 varies between approximately 0 t/hr and 22.5 t/hr. FIG. 3B shows an inverse relationship between flow through the water discharge port 202 and the height of the interface layer E. This inverse relationship is particularly evident from the increase in height of the interface layer (as evidenced by the general increases in density measurements) resulting from the decrease in flow through the water discharge port 202 at times $t_3$, $t_4$, $t_6$, and $t_7$ in FIG. 3B.

In FIG. 3C, the nuclear densitometer 118 again monitors the density of the fluid within the treater 104 over a period spanning approximately six days. During this time, as shown in FIG. 3C, the processor 114 records that the voltage of the electrostatic grid varies from approximately 0 V to approximately 15,000 V. FIG. 3C shows a strong direct relationship between voltage of the grid to the height of the interface layer, as alluded to above. This relationship is particularly evident at times $t_1$, $t_2$, and $t_3$ in FIG. 3C.

The data in FIGS. 3A-3C indicate that in order to lower the height of the interface layer in the treater 104, the processor 114 increases flow through the water discharge port 202 by opening or further opening the water discharge valve 106c. Analogously, in order to raise the height of the interface layer in the treater 104, the processor 114 decreases flow through the water discharge port 202 by closing or further closing the water discharge valve 106c. This helps to maintain a minimum water quality near the bottom of the treater 104 as well as to maintain a minimum density level near the top of the treater 104, as indicated by the voltage levels of the electrostatic grid. The processor 114 can analogously control the height of the interface layer E in the FWKO 102 or any other suitable vessel.

Figure 4:
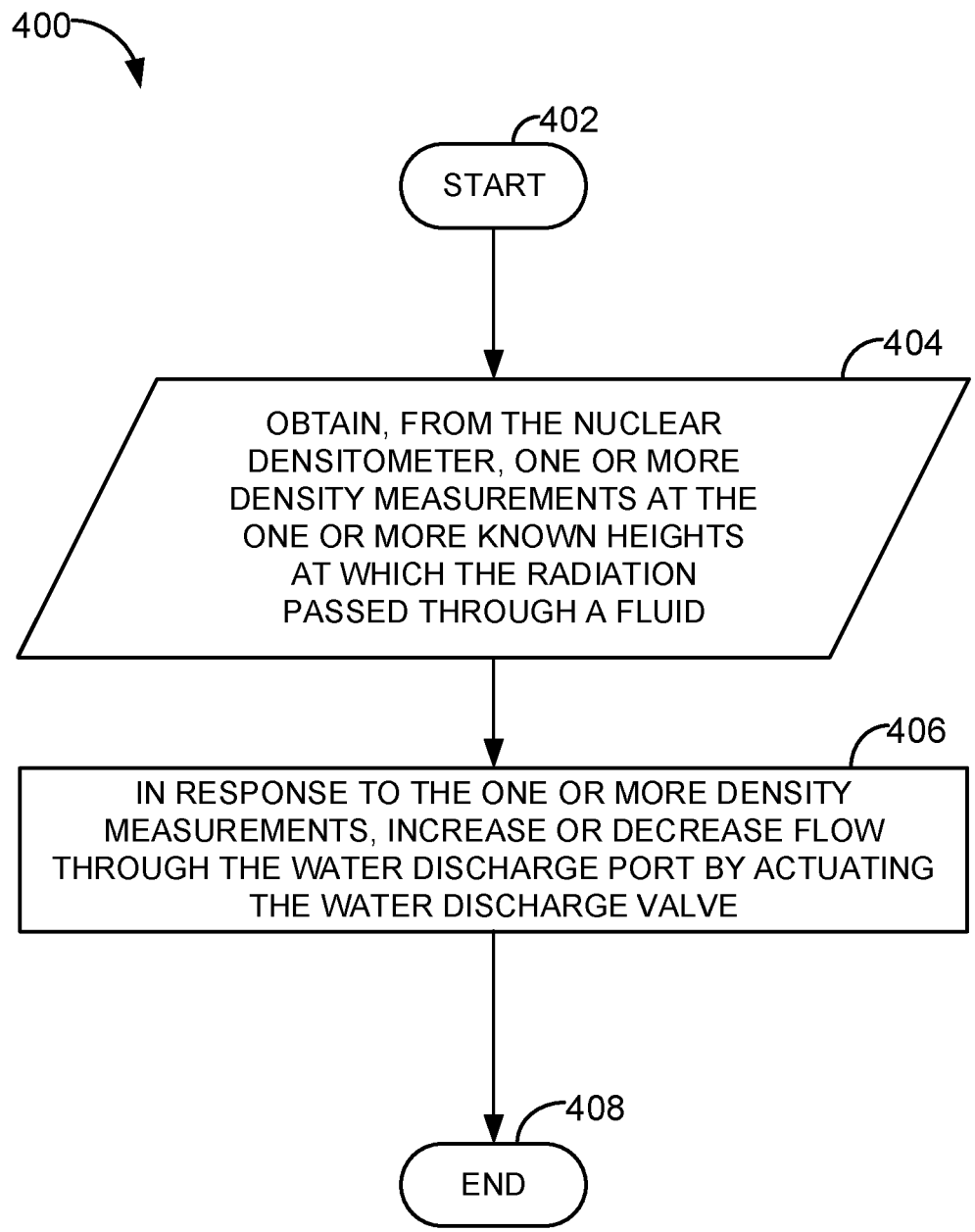
FIG. 4 is a method for adjusting the position of an oil-water interface layer, according to a third embodiment.

Referring now to FIG. 4, there is shown a method 400 for adjusting the position of an oil-water interface layer, according to another embodiment. The method 400 is stored as program code on the computer readable medium 116 and is performed by the processor 114. The processor 114 starts performing the method at block 402, and proceeds to block 404 where it obtains, from the nuclear densitometer 118, one or more density measurements at the one or more known heights at which the radiation passed through a fluid, which comprises the interface layer. When applied to the any of the FWKO 102 and treaters 104 shown in FIGS. 1, 2A, and 2B, the processor 114 receives density measurements obtained using at least one of the detectors 206a-e. The processor 114 then proceeds to block 406 where, in response to the one or more density measurements, it increases or decreases flow through the water discharge port 202 by actuating one or more of the water discharge valves 106.

Figure 5:
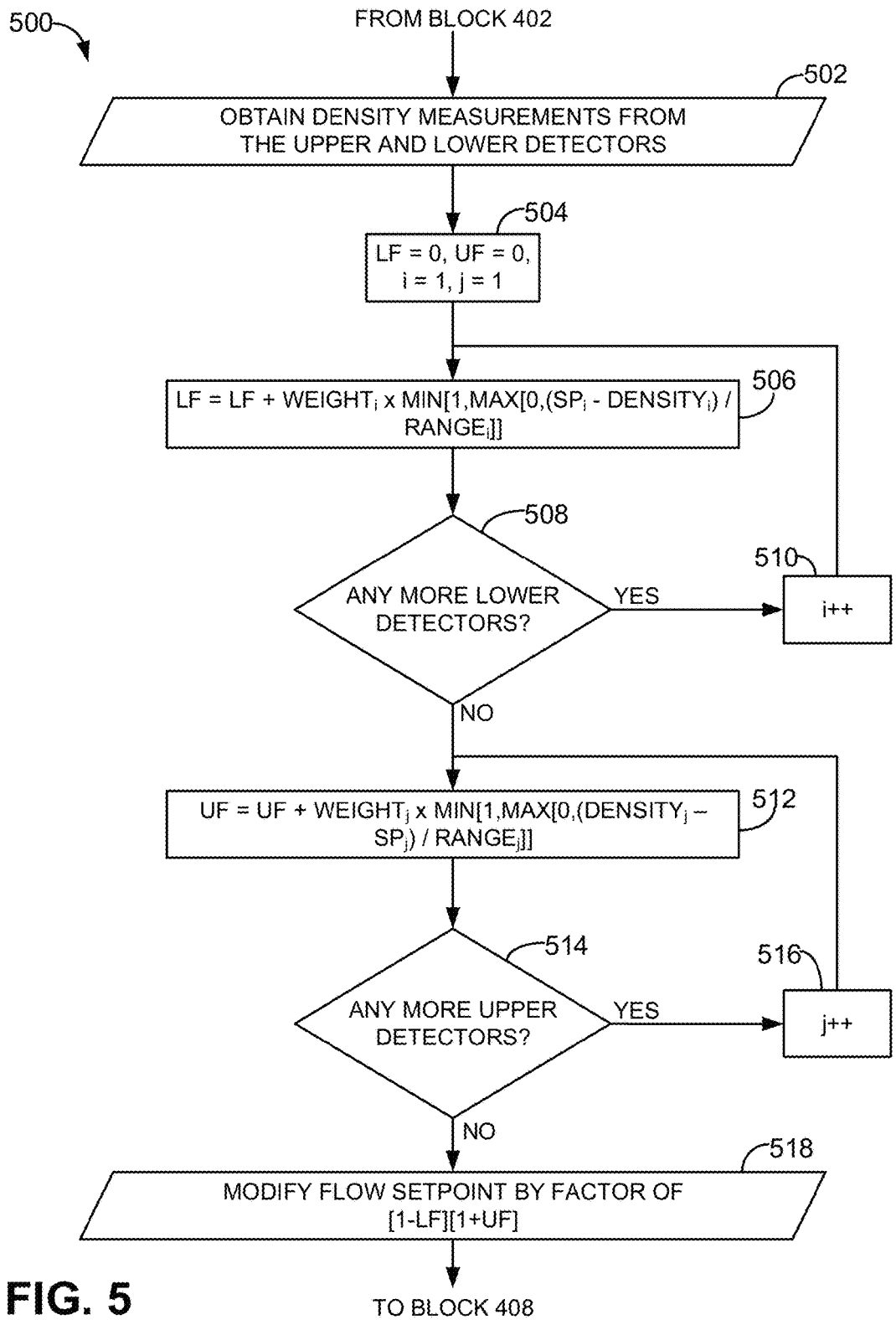
FIG. 5 is a method for adjusting the position of an oil-water interface layer, according to a fourth embodiment.

FIG. 5 depicts an embodiment of a method 500 for adjusting the position of an oil-water interface layer, according to another embodiment. The method 500 of FIG. 5 shown is one example of how to perform blocks 404 and 406 of FIG. 4.

In this description of the method 500, the embodiment of the nuclear densitometer 118 shown in FIGS. 2A and 2B is used, and the treaters 104 are used as an example vessel. Consequently, there are five nuclear detectors 206 of which the bottommost detector 206a and the second and third detectors 206b,c comprise the "lower detectors" and of which the fourth detector 206d and the uppermost detector 206e comprise the "upper detectors". As described in further detail below, the processor 114 uses the measurements obtained using the lower detectors 206a-c to determine a lower factor ("LF") that decreases an original flow setpoint through the treater 104 and uses the measurements obtained from the upper detectors 206d-e to determine an upper factor ("UF") that increases the original flow setpoint out of the treater 104. The "original flow setpoint" refers to the calculated setpoint of the flow of produced water out of the treater 104 through the water discharge port 202 before being altered in response to the density measurements. In alternative embodiments (not depicted), there may be any suitable number of detectors 206, with any subset of those detectors 206 comprising the "lower detectors" and any other subset of those detectors 206 comprising the "upper detectors". The subsets of the detectors 206 that comprise the lower and upper detectors may or may not be mutually exclusive.

The processor 114 at block 502 obtains density readings corresponding to heights $h_1$-$h_5$ of the treater 104 from the lower detectors 206a-c and upper detectors 206d,e. The processor 114 then proceeds to block 504 where it initializes variables for the LF and UF to zero, and for counting variables i and j to 1. The processor 114 then enters a loop comprising blocks 506, 508 and 510. At block 506, the processor performs Equation (1) for i=1, which represents the bottommost detector 206a:

$$LF = LF + \text{Weight}_i \times \text{MIN}\left[1, \text{MAX}\left[0, \frac{SP_i - \text{Density}_i}{\text{Range}_i}\right]\right] \quad (1)$$

where $\text{Weight}_i$ ("detector-specific weight") is a weight directly proportional to the degree the density measurement obtained using the lower detector 206a-c influences the flow through the water discharge port 202, $SP_i$ ("detector-specific density setpoint") is a water discharge density setpoint representing the ideal density measured by the lower detector 206a-c, $\text{Density}_i$ is the density obtained using the lower detector 206a-c, and $\text{Range}_i$ ("detector-specific range") is a density range inversely proportional to the degree $\text{Density}_i$ influences the flow through the water discharge port 202 when $\text{Density}_i$ deviates from $SP_i$ by less than $\text{Range}_i$ and wherein the $\text{Density}_i$ does not influence the flow through the water discharge port 202 when $\text{Density}_i$ deviates from $SP_i$ by at least $\text{Range}_i$.

One effect of Equation (1) is that if $\text{Density}_i$ is greater than $SP_i$, LF does not change. This is because a higher than expected $\text{Density}_i$ represents a greater proportion of water at $h_i$ than otherwise expected, which is beneficial in the context of discharging water from the treater 104.

After block 506, the processor 114 proceeds to block 508 where it determines whether there are any more lower detectors 206a-c. The first time performing the method 500, the answer is yes because there are a total of three lower detectors 206a-c and only the bottommost detector 206a has been considered by block 506. The processor 114 consequently proceeds to block 510 where it increments i and then returns to block 506 where it performs Equation (1) for i=2, the second detector 206b. The processor 114 subsequently proceeds through blocks 506, 508, and 510 another time to take into account i=3, the third detector 206c, and after i=3 proceeds from block 508 to block 512 because LF has been determined taking into account all of the lower detectors 206a-c. The effect of blocks 506, 508, and 510 is to determine LF by performing a summation over all the lower detectors 206a-c.

The processor 114 then begins determining OF by performing Equation (2) for j=1, which represents the first of the upper detectors 206d,e (i.e., the third detector 206d):

$$UF = UF + \text{Weight}_j \times \text{MIN}\left[1, \text{MAX}\left[0, \frac{\text{Density}_j - SP_j}{\text{Range}_j}\right]\right] \quad (2)$$

where $\text{Weight}_j$ is the detector-specific weight for the upper detector 206d,e, $SP_j$ is the detector-specific density setpoint, which for the upper detectors 206d,e is a sales oil density setpoint representing the ideal density measured by the upper detector 206d,e, $\text{Density}_j$ is the density obtained using the upper detector 206d,e, and $\text{Range}_j$ is the detector-specific density range inversely proportional to the degree $\text{Density}_j$ influences the flow through the water discharge port 202 when $\text{Density}_j$ deviates from $SP_j$ by less than $\text{Range}_j$ and wherein the $\text{Density}_j$ does not influence the flow through the water discharge port 202 when $\text{Density}_j$ deviates from $SP_j$ by at least $\text{Range}_j$. In embodiments of the method 500 in which voltage readings from the electrostatic grid are available, such as when the system 100 is applied to the treater 104, the sales oil density setpoint may be replaced with an electrostatic grid setpoint.

One effect of Equation (2) is that if $\text{Density}_i$ is less than $SP_j$, UF does not change. This is because a lower than expected $\text{Density}_i$ represents a greater proportion of oil at $h_i$ than otherwise expected, which is beneficial in the context of oil dehydration.

After block 512, the processor 114 proceeds to block 514 where it determines whether there are any more upper detectors 206d,e. The first time performing the method 500, the answer is yes because there are a total of two upper detectors 206d,e and only the fourth detector 206d has been considered by block 512. The processor 114 consequently proceeds to block 516 where it increments j and then returns to block 512 where it performs Equation (2) for j=2, the uppermost detector 206e. The processor 114 subsequently proceeds to block 514 again, where it determines there are no more upper detectors 206d,e, and accordingly proceeds to block 518. The effect of blocks 512, 514, and 516 is to determine UF by performing a summation over all the upper detectors 206d,e.

At block 518, the processor 114 determines the modified flow setpoint using Equation (3):

MODIFIED FLOW SETPOINT=(ORIGINAL FLOW SETPOINT)·[1−LF]·[1+UF] (3)

and then implements this modified flow setpoint by actuating the water discharge valve 106a,c accordingly. In another embodiment in which the treater 104 comprises n water discharge ports 202, Equation (3) may be replaced with Equation (3.1), below:

$$\text{MODIFIED FLOW SETPOINT} = \frac{1}{n} \cdot (\text{ORIGINAL FLOW SETPOINT}) \cdot [1 - LF] \cdot [1 + UF] \quad (3.1)$$

After modifying the treater's 104 flow setpoint, the processor 114 proceeds to block 408, where the method 500 ends.

In one embodiment, $\Sigma_i \text{Weight}_i=1$; additionally or alternatively, $\Sigma_j \text{Weight}_j=1$. Consequently, the processor 114 may shut the water discharge valve 106c completely in response to low density readings from the lower detectors 206a-c, and may increase the flow setpoint by as much as 100% in response to high density readings from the upper detectors 206d,e.

Embodiments Comprising One or Both of Temperature and Density Compensation

Figure 6:
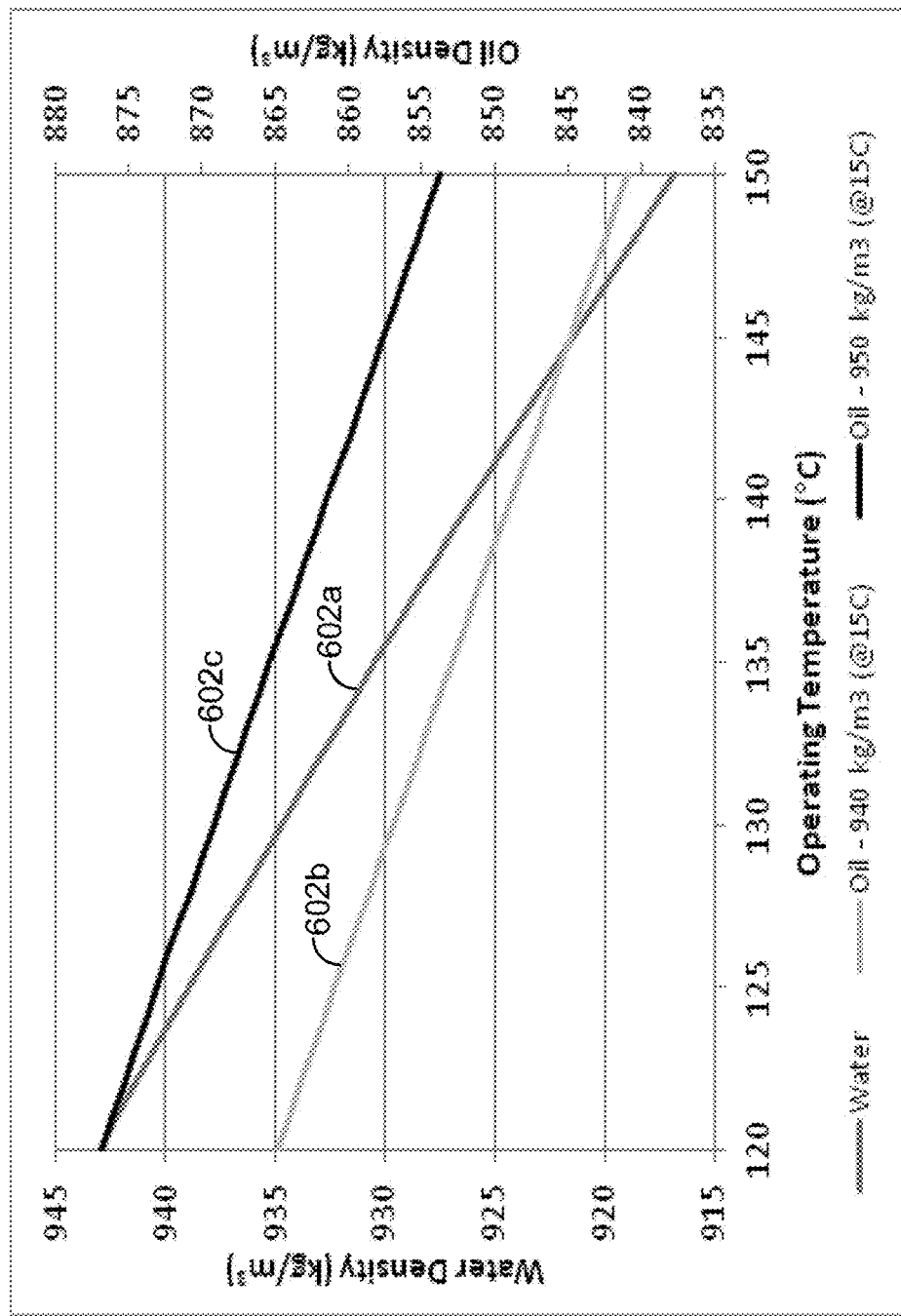
FIG. 6 is a graph depicting how the densities of water and oil change in response to changes in temperature.

In some embodiments, the methods 400,500 of FIGS. 4 and 5 may be modified to take into account changes in oil and water density measurements as a result of changes in one or both of the density of the oil phase of the production fluid fed into the vessel and temperature. For example, the temperature of the production fluid fed into the vessel may vary with environmental temperature changes due to season, while the density of the oil phase of the production fluid fed into the vessel may vary with the amount of diluent injected to the fluid upstream of the vessel or the nature of the raw materials (e.g., bitumen) from which the production fluid is produced. FIG. 6 depicts a graph 600 showing the effect temperature has on water and oil phase density. In particular, a first curve 602a depicts how water density decreases linearly with temperature from 120° C. to 150° C.; a second curve 602b depicts how the density of oil, which has a density of 940 kg/m³ at 15° C., decreases linearly with temperature from 120° C. to 150° C.; and a third curve 602c depicts how the density of oil, which has a density of 950 kg/m³ at 15° C., decreases linearly with temperature from 120° C. to 150° C.

Using the example above in which one of the treaters 104 is an example vessel to which the lower detectors 206a-c and the upper detectors 206d,e are mounted at heights $h_1$-$h_5$ of the treater 104, respectively, the processor 114 determines the corrected detector-specific density setpoint, $SP_i'$, for each of the lower detectors 206a-c using Equation (4) as follows:

$$SP_i' = [(T_{cal} - T_{treater}) \times c_{Temp}] + (SP_{i0} + \text{Offset}_i) \quad (4)$$

where $T_{cal}$ is the temperature of the treater 104 at the last time the lower detector 206a-c was calibrated, $T_{treater}$ is the measured operating temperature of the treater 104, $c_{temp}$ is an empirically determined correction factor for changes in emulsion density as a function of operating temperature, $SP_{i0}$ is an initial water discharge density setpoint prior to temperature correction being performed (i.e., the set point based on the configuration set at the last time the detector 206a-c was calibrated), and $\text{Offset}_i$ is a manual offset that a system operator may specify to adjust the corrected detector-specific density setpoint. In one embodiment, $\text{Offset}_i$ is limited to +/−5 kg/m³, although in different embodiments a different limit, or no limit, may be used. Additionally, while Equation (4) uses a single value for $T_{cal}$, $T_{treater}$, and $c_{Temp}$ for the entire treater 104, in different embodiments multiple values for one or more of $T_{cal}$, $T_{treater}$, and $c_{Temp}$ may be used; for example, a temperature sensor may be adjacent to each of the detectors 206a-c. $SP_i'$ for each of the detectors 206a-c may accordingly be determined using one or more of $T_{cal}$, $T_{treater}$, and $c_{Temp}$ specific for that detector 206a-c. An example value for $c_{Temp}$ in one embodiment is 0.8 kg/m³ per ° C., determined using density properties of water as well as dilbit.

Once $SP_i'$ for each of the lower detectors 206a-c is determined, the processor 114 may perform the method 500 of FIG. 5 using $SP_i'$ in place of $SP_i$ in Equation (1) to determine a temperature-corrected value for LF.

Again using the example in which one of the treaters 104 is an example vessel, the processor 114 determines the corrected detector-specific density setpoint, $SP_j'$, for each of the upper detectors 206d,e using Equation (5) as follows:

$$SP_j' = [(T_{cal} - T_{treater}) \times c_{Temp}] + [(\text{Density}_{vessel} - \rho_{cal}) \times c_{Densj}] + (SP_{j0} + \text{Offset}_j) \quad (5)$$

where $T_{cal}$ is the temperature of the treater 104 at the last time the upper detector 206d,e was calibrated, $T_{treater}$ is the measured operating temperature of the treater 104, $c_{temp}$ is an empirically determined correction factor for changes in emulsion density as a function of operating temperature, $\text{Density}_{vessel}$ is the dilbit treating density (i.e., density of the oil leaving the oil conduit 110 of the treater 104, also referred to as the "backend oil density") calculated based on process information upstream of the oil conduit 110, $\rho_{cal}$ is the measured backend oil density at the last time the upper detectors 206d,e were calibrated, $c_{Densj}$ is an empirically determined correction factor for changes in oil density as a function of operating temperature, $SP_{j0}$ is an initial sales oil density setpoint prior to temperature and density correction being performed (i.e., the set point based on the configuration set at the last time the detector 206d,e was calibrated), and $\text{Offset}_j$ is a manual offset that a system operator may specify to adjust the corrected detector-specific density setpoint. As with the lower detectors 206a-c, $\text{Offset}_j$ is limited to +/−5 kg/m³, although in different embodiments a different limit, or no limit, may be used. Additionally, while Equation (5) uses a single value for $T_{cal}$, $T_{treater}$, $c_{Temp}$, $\text{Density}_{vessel}$, and $\rho_{cal}$ for the entire treater 104, in different embodiments multiple values for one or more of $T_{cal}$, $T_{treater}$, $c_{Temp}$, $\text{Density}_{vessel}$, and $\rho_{cal}$ may be used; for example, a temperature sensor may be adjacent to each of the detectors 206a-c. $SP_j'$ for each of the detectors 206d,e may accordingly be determined using one or more of $T_{cal}$, $T_{treater}$, $c_{Temp}$, $\text{Density}_{vessel}$, and $\rho_{cal}$ specific for that detector 206d,e. An example value for $c_{Temp}$ in one embodiment is 0.8 kg/m³ per ° C., determined using density properties of water as well as dilbit, while an example value for $c_{Densj}$ is 1.2. In a further alternative embodiment, a measured value for $\text{Density}_{vessel}$ may be used in lieu of a calculated value, with the measured value obtained using, for example, a density sensor in the oil conduit 110.

Once $SP_j'$ for each of the upper detectors 206d,e is determined, the processor 114 may perform the method 500 of FIG. 5 using $SP_j'$ in place of $SP_j$ in Equation (2) to determine a temperature-corrected value for UF.

After the processor 114 determines corrected values for LF and UF, it may then proceed to determine a modified flow setpoint that takes into account one or both of temperature and density differences relative to the temperatures and densities measured when the detectors' 204 were calibrated. In some embodiments, the processor 114 may determine corrected detector-specific density setpoints for only the lower detectors 206a-c, only the upper detectors 206d,e, only a subset of the lower detectors 206a-c, only a subset of the upper detectors 206d,e, or a combination of a subset of the lower detectors 206a-c and a subset of the upper detectors 206d,e.

FIGS. 7A-8C depict experimental results obtained in which the processor 114 is configured to determine LF and UF using Equations (4) and (5) and data obtained from an embodiment of the nuclear densitometer 118 comprising eight detectors 206a-h located at heights $h_1$-$h_8$ on the treater 104. The height of the water discharge port 202<$h_1$, the height of the electrostatic grid>$h_8$, and $h_1$=600 mm, $h_2$=800 mm, $h_3$=1,000 mm, $h_4$=1,200 mm, $h_5$=1,400 mm, $h_6$=1,600 mm, $h_7$=1,800 mm, and $h_8$=2,000 mm.

Figure 7A:
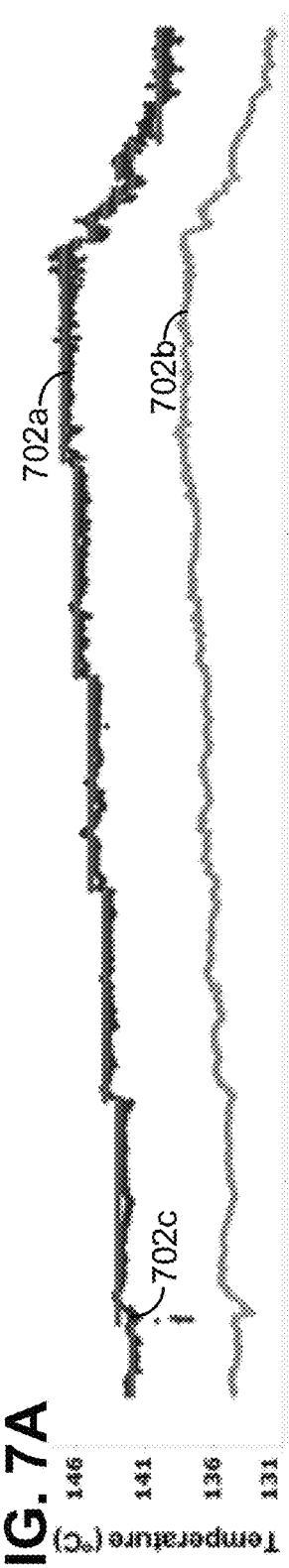
FIGS. 7A-7C are graphs depicting temperature upstream of and at the vessel, density measurements obtained using another embodiment of the system for adjusting the position of an oil-water interface layer installed on the vessel, and contribution made by various of the density measurements to the determination of how to adjust flow through the vessel's water discharge port.
Figure 7B:
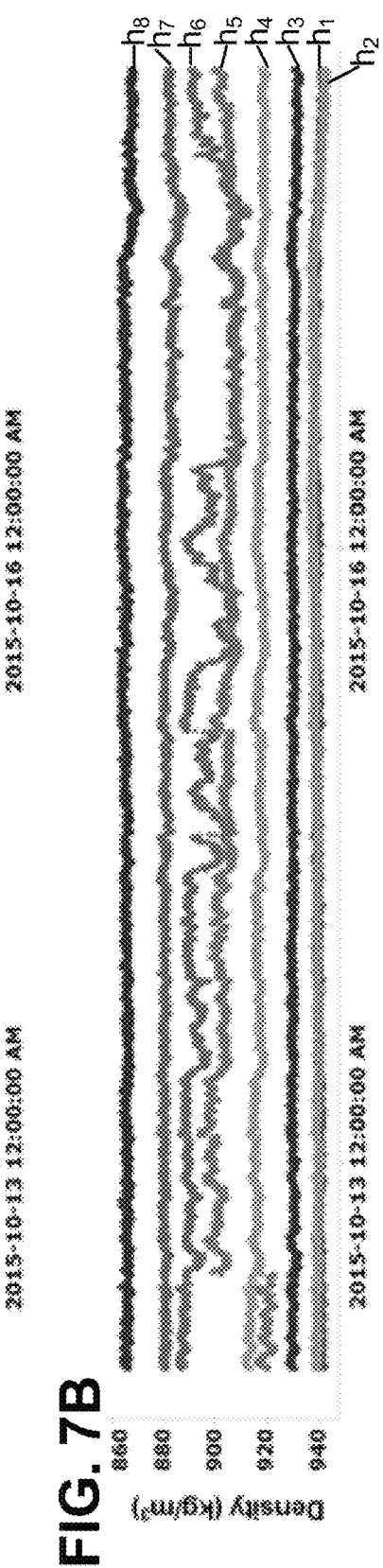
Figure 7C:
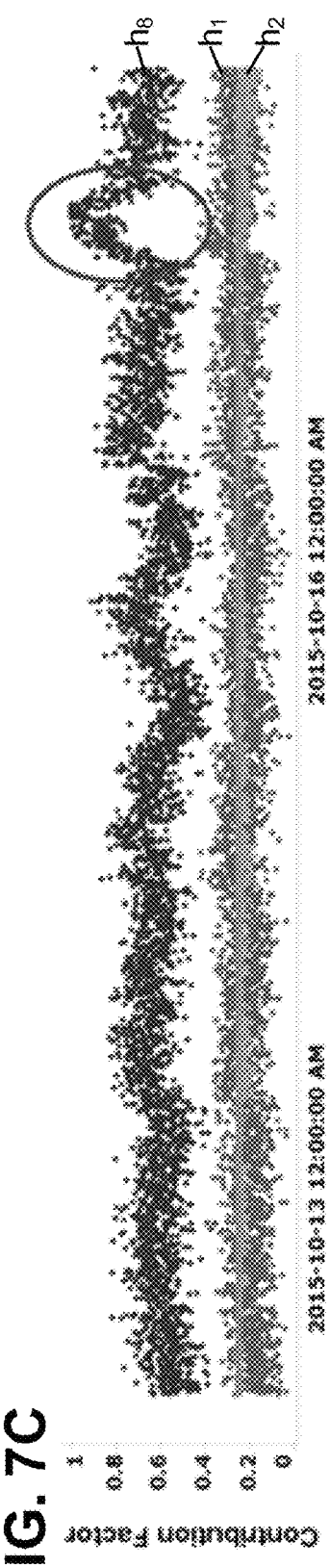

Referring in particular to FIGS. 7A-7C, FIG. 7A shows curves 702a-c, with a first curve 702a representing a temperature setpoint at a location upstream of the treater 104 and FWKO 102, a second curve 702b representing measured temperature at that upstream location, and a third curve 702c representing filtered and measured temperature of the treater 104 using a temperature sensor placed on the treater's 104 wall; FIG. 7B shows densitometer readings taken by the detectors 206 at heights $h_1$-$h_8$; and FIG. 7C shows the contribution to LF made by the two lowermost detectors 206a,b at heights $h_1$ and $h_2$ (i.e., the output of the rightmost term of Equation (1) for each of i=1 and i=2) and the contribution to OF made by the uppermost detector 206h at height hg (i.e., the output of the rightmost term of Equation (2) for the uppermost detector 206h). As shown in FIG. 7A, production fluid temperature upstream of the treater 104 is ramped down from 147° C. to 140° C. over the course of approximately 11.5 hours, and a moving average filter applied to the third curve 702c was set to have a window of two hours. The temperature filter was applied to smooth out small temperature bumps and to reduce the reaction time of the method performed by the processor 114. In another embodiment, the temperature filter may use a window with a different duration, such as thirty minutes.

As shown in FIG. 7B, notwithstanding the rapid change in temperature shown in FIG. 7A, the detectors 206 show a relatively stable interface layer E. Additionally, as shown in FIG. 7C, the contributions to LF by the bottommost two detectors 206a,b are relatively constant notwithstanding the significant temperature change. The deviation in contribution to UF by the uppermost detector 206h circled in FIG. 7C resulted from a lagging temperature filter, and was one factor in reducing the duration of the window used for the temperature filter from two hours in one embodiment to thirty minutes in another.

Referring now in particular to FIGS. 8A-8C, FIG. 8A shows a curve 802 of calculated backend density of the oil exiting the oil conduit 110, FIG. 8B shows densitometer readings taken by the detectors 206 at heights $h_1$-$h_8$, while FIG. 8C shows the contribution to LF made by the three lowermost detectors 206a-c at heights $h_1$-$h_3$ (curve 804) (i.e., LF determined using Equation (1) for i=1 to i=3) and the contribution to UF made by the uppermost detector 206h at height hg (curve 806). The shaded portions of FIGS. 8A-8C represent a period during which a reduced amount of diluent is added to the production fluid, consequently increasing backend density. As shown in FIG. 8C, in this embodiment the processor 114 limits the effect of the increase in backend treating density to the oil phase and helps to ensure that the water phase remains stable.

Examples of Additional Alternative Embodiments

While FIG. 5 depicts one example embodiment in which the detectors 206 are used to determine whether to increase or lower the interface layer, alternative embodiments (not depicted) are possible.

In one example alternative embodiment, the processor 114 may consider only density measurements from one or more lower detectors 206 and not consider any measurements obtained using any upper detectors 206. In this embodiment, the processor 114 could be used to lower the original flow setpoint, but not to increase it. Conversely, in another example embodiment, the processor 114 may consider only density measurements from one or more upper detectors 206 and not consider any measurements obtained using any lower detectors 206. In this embodiment, the processor 114 could be used to increase the original flow setpoint, but not to decrease it.

In another alternative embodiment, the LF and UF may be determined differently, and may modify the original flow setpoint in a manner different than in Equation (3). For example, in embodiments in which it is of paramount importance that oil concentrations in the water leaving the vessel be minimized, if LF>0 then the processor 114 may ignore any changes to the flow setpoint that otherwise would result from considering UF. Conversely, in embodiments in which it is of paramount important that sales oil volume be maximized, if UF>0 then the processor 114 may ignore any changes to the flow setpoint that otherwise would result from considering LF.

In additional alternative embodiments, weighting totals may be modified to change the interaction between the UF and LF described in Equation (3) to generate a different response from the control scheme. For example, a higher UF weight ($\Sigma_j$ Weight$_j$>1) may allow for more aggressive water discharge flows; additionally or alternatively, a lower LF weight ($\Sigma_i$ Weight$_i$<1) may stop the water discharge valve 106c from completely shutting and therefore give greater importance to oil quality at the potential expense of water quality.

As mentioned above in respect of FIG. 1, further embodiments include an apparatus for adjusting the position of an oil-water interface layer. The apparatus may comprise a system controller, with the controller comprising the processor 114 communicatively coupled with the non-transitory computer readable medium 116 that has stored thereon program code that, when executed by the processor, causes the processor to perform the methods 400,500 of FIGS. 4 and 5, including those embodiments in which the methods 400,500 use Equations (4) and (5) to compensate for one or both of temperature and density variations. Some embodiments of the apparatus may further comprise the nuclear densitometer 118, with the densitometer 118 communicatively coupled to the controller.

In additional alternative embodiments, the interface layer A need not be an oil-water interface layer. Instead of oil and water, for example, two normally immiscible fluids of different densities may be used, and those fluids may enter the vessel emulsified.

The processor 114 used in the foregoing embodiments may be, for example, a microprocessor, microcontroller, programmable logic controller, field programmable gate array, or an application-specific integrated circuit. Examples of computer readable media are non-transitory and include disc-based media such as CD-ROMs and DVDs, magnetic media such as hard drives and other forms of magnetic disk storage, semiconductor based media such as flash media, random access memory (including DRAM and SRAM), and read only memory.

It is contemplated that any part of any aspect or embodiment discussed in this specification can be implemented or combined with any part of any other aspect or embodiment discussed in this specification.

For the sake of convenience, the example embodiments above are described as various interconnected functional blocks. This is not necessary, however, and there may be cases where these functional blocks are equivalently aggregated into a single logic device, program or operation with unclear boundaries. In any event, the functional blocks can be implemented by themselves, or in combination with other pieces of hardware or software.

While particular embodiments have been described in the foregoing, it is to be understood that other embodiments are possible and are intended to be included herein. It will be clear to any person skilled in the art that modifications of and adjustments to the foregoing embodiments, not shown, are possible.

The invention claimed is:

1. A system for adjusting a position of an oil-water interface layer, the system comprising:
   a vessel for containing a fluid comprising the oil-water interface layer and comprising a water discharge port and a fluid outlet, the fluid outlet being higher on the vessel than the water discharge port;
   a nuclear densitometer positioned to emit radiation into the fluid and to measure the radiation after it has passed through the fluid, wherein the radiation passes through the fluid at at least two known heights of the fluid, wherein the nuclear densitometer comprises one or more nuclear sources extending vertically along one of an inside or outside of the vessel and at least two nuclear detectors located on the other of the inside or outside of the vessel at the known heights;

a water discharge valve positioned to control flow through the water discharge port;

a controller communicatively coupled to the nuclear densitometer and to the water discharge valve, the controller configured to perform a method comprising:

obtaining, from the nuclear densitometer, at least two density measurements at the known heights at which the radiation passed through the fluid;

in response to the density measurements, increasing or decreasing flow through the water discharge port by actuating the water discharge valve;

for each of the density measurements, comparing the density measurement to a water discharge density setpoint specific to the detector used to obtain the density measurement ("detector-specific density setpoint"); and decreasing the flow through the water discharge port in response to how much each of the density measurements is less than the detector-specific density setpoint.

2. The system of claim 1 wherein each of the detectors used to obtain the density measurements is associated with a weight ("detector-specific weight"), accessible by the controller, directly proportional to the degree the density measurement obtained using the detector influences the flow through the water discharge port.

3. The system of claim 2 wherein each of the detectors used to obtain the density measurements is associated with a density range ("detector-specific density range"), accessible by the controller, inversely proportional to the degree the density measurement obtained using the detector influences the flow through the water discharge port when the density measurement deviates from the detector-specific density setpoint by less than the detector-specific density range and wherein the density measurement obtained using the detector does not influence the flow through the water discharge port when the density measurement deviates from the detector-specific density setpoint by at least the detector-specific density range.

4. The system of claim 1 wherein the detector-specific density setpoint is determined from an initial detector-specific density setpoint, determined at a previous calibration, that is offset by a value proportional to a difference between a current temperature of the vessel and a temperature of the vessel obtained at the previous calibration.

5. A system for adjusting a position of an oil-water interface layer, the system comprising:

a vessel for containing a fluid comprising the oil-water interface layer and comprising a water discharge port and a fluid outlet, the fluid outlet being higher on the vessel than the water discharge port;

a nuclear densitometer positioned to emit radiation into the fluid and to measure the radiation after it has passed through the fluid, wherein the radiation passes through the fluid at at least two known heights of the fluid, wherein the nuclear densitometer comprises one or more nuclear sources extending vertically along one of an inside or outside of the vessel and at least two nuclear detectors located on the other of the inside or outside of the vessel at the known heights;

a water discharge valve positioned to control flow through the water discharge port;

a controller communicatively coupled to the nuclear densitometer and to the water discharge valve, the controller configured to perform a method comprising:

obtaining, from the nuclear densitometer, at least two density measurements at the known heights at which the radiation passed through the fluid;

in response to the density measurements, increasing or decreasing flow through the water discharge port by actuating the water discharge valve;

for each of the density measurements, comparing the density measurement to a sales oil density setpoint specific to the detector used to obtain the density measurement ("detector-specific density setpoint"); and increasing the flow through the water discharge port in response to how much each of the density measurements is greater than the detector-specific density setpoint.

6. The system of claim 5 wherein each of the detectors used to obtain the density measurements is associated with a weight ("detector-specific weight"), accessible by the controller, directly proportional to the degree the density measurement obtained using the detector influences the flow through the water discharge port.

7. The system of claim 6 wherein each of the detectors used to obtain the density measurements is associated with a density range ("detector-specific density range"), accessible by the controller, inversely proportional to the degree the density measurement obtained using the detector influences the flow through the water discharge port when the density measurement deviates from the detector-specific density setpoint by less than the detector-specific density range and wherein the density measurement obtained using the detector does not influence the flow through the water discharge port when the density measurement deviates from the detector-specific density setpoint by at least the detector-specific density range.

8. The system of claim 5 wherein, for one or more upper detectors located above a lowest one of the detectors, the detector-specific density setpoint is determined from an initial detector-specific density setpoint, determined at a previous calibration, that is offset by a value proportional to one or both of a difference between:

a current temperature of the vessel and a temperature of the vessel obtained at the previous calibration; and a current density of oil exiting the vessel and a density of oil exiting the vessel obtained at the previous calibration.

9. A method for adjusting a position of an oil-water interface layer, the method comprising:

obtaining, from a nuclear densitometer positioned to emit radiation at at least two known heights into a vessel containing a fluid comprising the interface layer and to measure the radiation after it has passed through the fluid, at least two density measurements of the fluid at the known heights, wherein the nuclear densitometer comprises one or more nuclear sources extending vertically along one of an inside or outside of the vessel and at least two nuclear detectors located on the other of the inside or outside of the vessel at the known heights;

in response to the density measurements, increasing or decreasing flow through a water discharge port comprising part of the vessel;

for each of the density measurements, comparing the density measurement to a water discharge density setpoint specific to the detector used to obtain the density measurement ("detector-specific density setpoint"); and decreasing the flow through the water discharge port in response to how much each of the density measurements is less than the detector-specific density setpoint.

10. The method of claim 9 wherein each of the detectors used to obtain the density measurements is associated with a weight ("detector-specific weight") directly proportional to the degree the density measurement obtained using the detector influences the flow through the water discharge port.

11. The method of claim 10 wherein each of the detectors used to obtain the density measurements is associated with a density range ("detector-specific density range") inversely proportional to the degree the density measurement obtained using the detector influences the flow through the water discharge port when the density measurement deviates from the detector-specific density setpoint by less than the detector-specific density range and wherein the density measurement obtained using the detector does not influence the flow through the water discharge port when the density measurement deviates from the detector-specific density setpoint by at least the detector-specific density range.

12. The method of claim 9 wherein the detector-specific density setpoint is determined from an initial detector-specific density setpoint, determined at a previous calibration, that is offset by a value proportional to a difference between a current temperature of the vessel and a temperature of the vessel obtained at the previous calibration.

13. A method for adjusting a position of an oil-water interface layer, the method comprising:

obtaining, from a nuclear densitometer positioned to emit radiation at at least two known heights into a vessel containing a fluid comprising the interface layer and to measure the radiation after it has passed through the fluid, at least two density measurements of the fluid at the known heights, wherein the nuclear densitometer comprises one or more nuclear sources extending vertically along one of an inside or outside of the vessel and at least two nuclear detectors located on the other of the inside or outside of the vessel at the known heights;

in response to the density measurements, increasing or decreasing flow through a water discharge port comprising part of the vessel;

for each of the density measurements, comparing the density measurement to a sales oil density setpoint specific to the detector used to obtain the density measurement ("detector-specific density setpoint"); and increasing the flow through the water discharge port in response to how much each of the density measurements is greater than the detector-specific density setpoint.

14. The method of claim 13 wherein each of the detectors used to obtain the density measurements is associated with a weight ("detector-specific weight") directly proportional to the degree the density measurement obtained using the detector influences the flow through the water discharge port.

15. The method of claim 14 wherein each of the detectors used to obtain the density measurements is associated with a density range ("detector-specific density range") inversely proportional to the degree the density measurement obtained using the detector influences the flow through the water discharge port when the density measurement deviates from the detector-specific density setpoint by less than the detector-specific density range and wherein the density measurement obtained using the detector does not influence the flow through the water discharge port when the density measurement deviates from the detector-specific density setpoint by at least the detector-specific density range.

16. The method of claim 13 wherein, for one or more upper detectors located above a lowest one of the detectors, the detector-specific density setpoint is determined from an initial detector-specific density setpoint, determined at a previous calibration, that is offset by a value proportional to one or both of a difference between:

a current temperature of the vessel and a temperature of the vessel obtained at the previous calibration; and a current density of oil exiting the vessel and a density of oil exiting the vessel obtained at the previous calibration.

* * * * *